(12) United States Patent
Roosenboom et al.

(10) Patent No.: US 9,220,242 B2
(45) Date of Patent: Dec. 29, 2015

(54) METHOD AND DEVICE FOR MONITORING MOVEMENTS OF AN ANIMAL

(75) Inventors: Derk Jan Roosenboom, Haaksbergen (NL); Jeroen Martin van Dijk, Enschede (NL); Egbert Gert Jan Uninge, Twello (NL)

(73) Assignee: N.V. NEDERLANDSCHE APPARATENFABRIEK NEDAP, Groenlo (NL)

( * ) Notice: Subject to any disclaimer, the term of this patent is extended or adjusted under 35 U.S.C. 154(b) by 566 days.

(21) Appl. No.: 13/445,068

(22) Filed: Apr. 12, 2012

(65) Prior Publication Data
US 2012/0262295 A1    Oct. 18, 2012

(30) Foreign Application Priority Data

Apr. 13, 2011    (NL) ..................................... 2006598

(51) Int. Cl.
G08B 23/00    (2006.01)
G08B 1/08    (2006.01)
(Continued)

(52) U.S. Cl.
CPC ............. *A01K 29/005* (2013.01); *A61B 5/1112* (2013.01); *A61B 5/1118* (2013.01); *A61B 5/1123* (2013.01); *A01K 15/023* (2013.01); *A61B 2503/40* (2013.01)

(58) Field of Classification Search
CPC ... A01K 29/005; A01K 29/00; A01K 11/006; A01K 15/023; A01K 11/008; A01K 27/009; A61B 2503/40; A61B 5/1118; A61B 5/1123; A61B 5/1105; A61N 1/08; A61N 1/37; G06Q 10/08; G06Q 10/0833; G08B 21/0252; G08B 21/0288; G08B 23/00; G06F 19/3418

USPC ........ 340/573.1, 573.3, 539.13, 540, 539.11, 340/539.23, 539.21, 687, 568.1; 119/174, 119/14, 719, 720, 721, 851, 908, 421, 859; 342/357.63, 357.71, 357.74
See application file for complete search history.

(56) References Cited

U.S. PATENT DOCUMENTS

2005/0145187 A1*    7/2005    Gray ............................. 119/174
2007/0171047 A1*    7/2007    Goodman et al. ........ 340/539.13
(Continued)

FOREIGN PATENT DOCUMENTS

EP    0 959 672    3/2003
EP    2510783 B1    10/2013
(Continued)

*Primary Examiner* — Mirza Alam
(74) *Attorney, Agent, or Firm* — Jacobson Holman, PLLC.

(57) ABSTRACT

A method for monitoring movements of an animal, wherein the animal is provided with a device having sensor means for detecting movements, and generating at least a signal with information about detected movements of the animal. The device is further provided with a control unit for processing the information in the signal and for storing the processed information and transmitter means for transmitting information stored in the control unit. The method comprises: storing in the control unit a number of predetermined-type movements counted during a predetermined set of periods which comprises a number of successive first periods, and transmitting a number of the stored numbers of counted movements at moments which depend on the number of detected predetermined-type movements in at least one of the past first periods and/or depend on at least one of the stored orientations of the sensor means.

61 Claims, 2 Drawing Sheets

Figure 1:
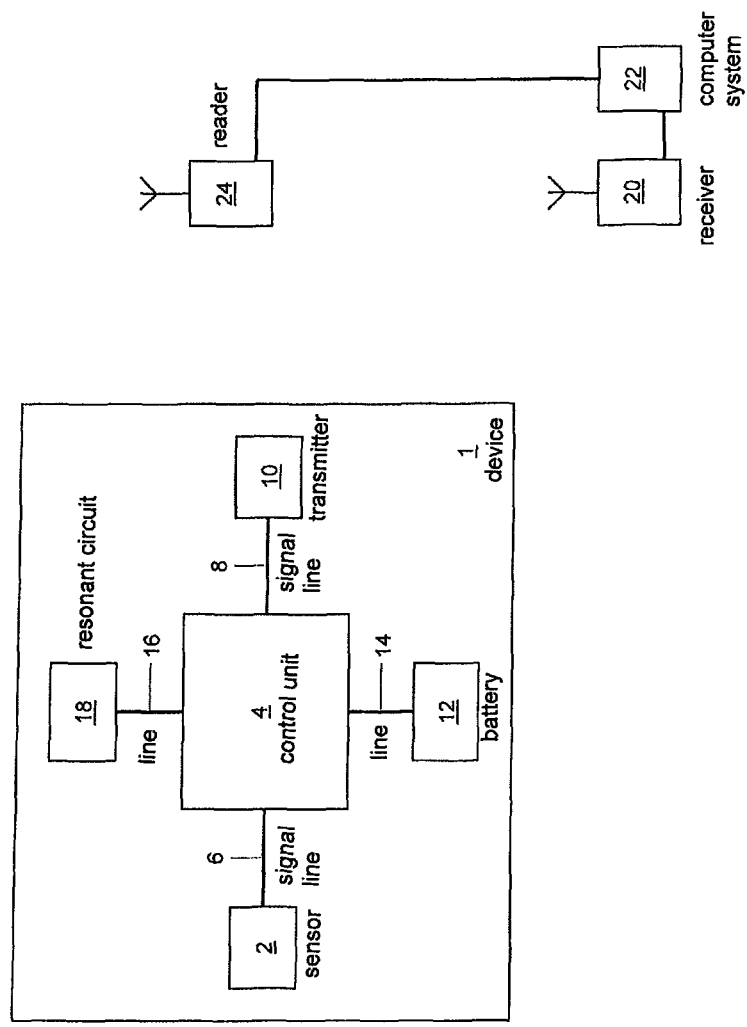

(51) Int. Cl.
*A01K 15/04* (2006.01)
*A01K 1/03* (2006.01)
*A01K 29/00* (2006.01)
*A61B 5/11* (2006.01)
*A01K 15/02* (2006.01)

(56) References Cited

U.S. PATENT DOCUMENTS

2008/0035072 A1* 2/2008 Lee .................. 119/720

2009/0276012 A1* 11/2009 Hyde et al. .................. 607/60
2010/0321189 A1* 12/2010 Gibson .................. 340/573.3
2013/0014706 A1* 1/2013 Menkes .................. 119/859

FOREIGN PATENT DOCUMENTS

WO 91/11678 8/1991
WO 2011/010922 1/2011

* cited by examiner

METHOD AND DEVICE FOR MONITORING MOVEMENTS OF AN ANIMAL

This application claims the priority of The Netherlands no. 2006598 filed Apr. 13, 2011, hereby incorporated by reference.

The invention relates to a method for monitoring movements of an animal such as a cow or pig, wherein the animal is provided with a device provided with sensor means for detecting movements of the animal, optionally also for detecting an orientation of the sensor means, and generating at least a signal comprising information about detected movements of the animal and optionally also comprising information about detected orientations, a control unit for processing the information in the signal and for storing the processed information and transmitter means for transmitting information stored in the control unit.

Such a method is known from EP 0 959 672 B1. In the known method, at periodically repeated times having between them a first time interval of a first predetermined length of 14 sec., it is determined whether the animal has adopted a predetermined particular state. If an animal has adopted such a state, a counter value is incremented, indicating the number of first time intervals in which it has been detected that the respective animal has adopted the state concerned. Also, at periodically repeated times having time intervals between them of a second predetermined length greater than the first predetermined length, information about the number of counted time intervals of the first predetermined length is transmitted by the transmitter.

A disadvantage of the known device is that it is only detected whether during the time interval of the first predetermined length the animal has or has not adopted at least one predetermined particular state. If the animal has adopted the predetermined particular state once, twice or several times, it is only registered that the animal in the respective time interval of a predetermined first length has adopted the predetermined particular state at least once. As a consequence, relevant information about the movement performed by the animal is lost. A further disadvantage is that transmission of the collected information always takes place with a frequency lower than the frequency with which information about the movements of the animal is stored. This means that, particularly when the animal performs movements during successive periods of the first predetermined length, the information about these movements is transmitted with a relatively low frequency and hence with a delay with respect to the current situation.

The invention contemplates providing a solution to at least a number of the disadvantages mentioned. According to the invention, the method comprises the following method steps:
a. at periodically repeated moments, registering with the control unit the signal determined with the sensor means;
b. on the basis of signals registered during a first predetermined period which comprises a multiplicity of method steps a., detecting with the control unit movements of a predetermined type, such as steps of an animal, and determining the number of movements of the predetermined type that occurred during the first period;
c. repeating the method step b. for a multiplicity of successive predetermined first periods;
d. storing in the control unit the number of predetermined-type movements counted during a predetermined set of periods which comprises a number of successive first periods, optionally in combination with storing at least one orientation of the sensor means which has been measured during the predetermined number of successive first periods of the set;
e. repeating step d. for successive predetermined sets of first periods;
f. transmitting a number of the stored numbers of counted movements at moments which depend on the number of detected predetermined-type movements in at least one of the past first periods and/or depend on at least one of the stored orientations of the sensor means.

As in step b. the number of movements of the predetermined type that occur during the first predetermined period is detected while in step d. the number of predetermined-type movements counted during a predetermined set comprising a number of successive first periods is stored, no information is lost about the number of movements of the predetermined type detected with the device. If the predetermined set of periods in each case comprises one first predetermined period, this means that for each first period it is stored how many movements of a predetermined type have been counted in that respective first period. If the predetermined set of periods comprises, for example, three successive first predetermined periods, it is stored each time for a combination of three successive first predetermined periods how many movements of the predetermined type have been counted. In either case no information about the number of detected movements of the predetermined type is lost.

Further, it holds according to the invention that transmission of a number of the stored numbers of counted movements is carried out at moments which depend on the number of detected predetermined-type movements in at least one of the past first predetermined periods and/or which depend on at least one of the stored orientations of the sensor means. If, for example, in at least one of the past first periods no movements of a first type have been detected, transmission of a number of the stored numbers of counted movements can be postponed because no new counts have been added anyway. On the receiving side, such postponement can be rightly interpreted as a recent absence of any detection of movements of the predetermined type. On the other hand, such postponement cannot last too long because this could give rise to the idea on the receiving side that the device is not transmitting any information because it is broken, or that the device is beyond reach of the receiving side. That is why it preferably holds that the length of a second period between successive moments at which stored numbers of counted movements are transmitted in dependence on the number of detected predetermined-type movements in at least one of the past first periods and/or in dependence on at least one of the stored orientations of the sensor means can vary from a first duration to a second duration, wherein the second duration is greater than the first duration. The length of the second period between successive moments at which stored numbers of counted movements are transmitted can thus, according to this example, vary from a first duration to a second duration. The first and second durations are preferably predetermined. In particular, the first and second durations are each fixed. More particularly, it holds that the duration of each predetermined first period is fixed. Preferably, it holds, for example, that the duration of each predetermined first period is equal to the first duration. Also, it preferably holds that the second duration is equal to or less than three times the first duration. More particularly, it holds that the first duration is about 5 minutes and that the second duration is about 15 minutes. This means, then, that it holds, in particular, that the first predetermined period in each case covers a duration of 5 minutes while the second period has a length that may vary from 5-15 minutes, in dependence on, for example, the number of detected movements within at least one past first period as discussed above.

Transmission of a number of the stored numbers of counted movements at moments which depend on the number of detected predetermined-type movements in at least one of the past first periods can be carried out in different manners. The respective dependence on the number of detected movements of the predetermined type can for instance reside in the fact whether the number in the last first period is equal to 0 or whether the number is greater than or equal to 1. Steering by this above-mentioned number can hence entail, e.g., looking at the magnitude of the number of movements of the predetermined type that have been detected in the last first period, and seeing, for example, whether this number is 0 or whether this number is greater than 0. If the number is 0 the frequency with which step f. is carried out (i.e., the repeat frequency with which step f. is carried out) can be lowered. This means that the length of the coming second period is augmented. If the number is 1 or greater than 1, the frequency with which step f. is carried out can be raised. This means that the length of the coming second period is reduced. Such dependence can practically be realized in that the control unit, for a past first period, places in its memory a flag indicating that in the respective first period more than one movement has been detected. If a respective past period is provided with a flag, then step f. is carried out relatively soon (for example, 5 minutes) after the last step f. is carried out. If the respective past first period is not provided with a flag, then step f. can be carried out relatively less soon (for example, 15 minutes) after the last step f. is carried out. It is also possible, however, that the frequency with which step f. is carried out depends on the fact whether in the past first period 0, 1 or more than 1 movements of the predetermined type have been detected. If the number is equal to 0, for example, step f. is carried out 15 minutes after step f. has been carried out last, if the number is equal to 1, for example, step f. is carried out 10 minutes after step f. has been carried out last, and if the number is more than 1, for example, step f. is carried out 5 minutes after step f. has been carried out last.

According to a preferred embodiment, it holds that step f. is carried out following a second period having a length equal to the second duration and in which no movements of the predetermined type have been detected and that step f. is also carried out following a second period having a length equal to the first duration and in which at least one movement of the predetermined type has been detected.

In this exemplary embodiment, therefore, transmission of information is initiated following the second period having a length equal to the second duration (for example, 15 minutes) if no movements of the predetermined type have been detected in the respective second period. On the other hand, step f. is also carried out following a second period having a length equal to the first duration (for example, 5 minutes) when in the respective second period movements of the predetermined type have been detected.

For this specific embodiment, too, it holds that after a detected movement of the animal, step f. is carried out relatively soon because step f. is carried out following a second period having a length equal to the first duration (for example, 5 minutes). Furthermore, it holds that step f. is carried out with a relative delay when for a while no predetermined movement of the animal is detected, because step f. is carried out following a second period having a length equal to the second duration (for example, 15 minutes) if no movements of the predetermined type have been detected in this second period. Thus energy for transmission can be saved.

According to a highly advanced embodiment, it holds that the method step f. is not carried out anymore if during a third period having a predetermined length which is longer than the second duration no movements of the predetermined type have been detected. The third period can have a length of, for example, 2-24 hours, preferably of 4-12 hours, more preferably of 6-10 hours and still more preferably of 8 hours. This means, for example, that when an animal does not move anymore because it is dead or when the device is not used anymore because it is stored in, for example, a cupboard, the device will not transmit at all anymore after 8 hours, so that, at least almost, no energy is consumed.

According to a preferred embodiment, it holds furthermore that step f. is always carried out at a moment when the movement of the predetermined type has been detected while during the period preceding that moment which is longer than the first duration no step f. has been carried out. Such a situation can occur, for example, when the animal has not moved for a while, as a result of which the second period has had a length of the second duration (for example, 15 minutes). When the animal then suddenly starts moving again, step f. is carried out directly. This also applies when step f. was not carried out at all anymore because during a third period no movements of the predetermined type had been detected. So, if the device sits in storage in, for example, a cupboard and is taken out to be used, it will immediately be activated again.

In each of the above-outlined embodiments it holds, preferably, that the first periods are contiguous to each other.

When in a farm a multiplicity of such devices are used simultaneously, the chances are low that these devices will interfere with each other because, as set out above, the step f., i.e., the transmission of the information, is carried out according to an irregular, not predictable time pattern. This is because the pattern depends on the detected movements and/or the detected orientation. The irregularity in the pattern can be augmented when, according to a preferred embodiment, it holds that at least one of the first duration and the second duration is randomly selected by the control unit. This random selection can take place, for example, right after step f. has been carried out. Preferably, it holds here that the selection of the first duration is within a predetermined range and the selection of the second duration is within a predetermined range. The first range may for instance be equal to 3-7 minutes, and the second range may for instance be equal to 10-20 minutes.

In particular, it holds that with the transmission in step f., also transmission of an identification code stored in the control unit is carried out. In this manner, for instance, it is known on the receiving side to which animal the received information relates. The movement of the predetermined type which is detected in step b. can be a variety of types of movement, such as a step of an animal or a movement of the head or neck of the animal. It is known per se how such predetermined-type movements can be detected from signals coming from the sensor means.

In particular, it holds that in step f. a multiplicity of the stored numbers of counted movements of the predetermined type are transmitted, in particular a number that relates to a total period having a length of 12-26 hours, more preferably a number corresponding to a total period of 24 hours. This provides the advantage that when on the receiving side reception of information transmitted in a step f. has been missed, this information is generally transmitted once again in a next step f., so that the chances are low that information is transmitted and is not received. If, for example, it holds that step d. comprises a set of three successive periods, this means that, for example, every 15 minutes the detected number of movements is stored in the control unit. If in step f. a multiplicity of the stored numbers of counted movements are transmitted that relate to the total period of 24 hours, this means that in step f. each time 96 detected numbers are transmitted, each time relating to the last 24 hours.

In particular, it holds furthermore that step f. may also be carried out in dependence on a detected orientation of the sensor means. When, for example, it is detected that the animal assumes an orientation that corresponds to lying, and when such lying persists longer than, for example, a fourth predetermined period, step f. is not carried out anymore after this fourth predetermined period. Such a situation can occur, for example, when an animal is dead, as a result of which a lying orientation of the animal is measured continuously. The fourth period may be chosen to be, for example, equal to the third period and is thus, for example, equal to 8 hours.

According to a variant, it holds that step f. is also carried out following the second period having a length which is equal to one or more times the first duration and which is less than the second duration while in this second period at least one movement of the predetermined type has been detected. This variant can be applied with advantage when it actually does not hold that step f. is always carried out at a moment when the movement of the predetermined type has been detected while during the period preceding that moment which is longer than the first duration, no step f. has been carried out.

The invention also relates to a device for monitoring the movement of the animal such as a cow or a pig, wherein the device is arranged to be attached to the animal and is provided with sensor means for detecting movements of the animal, optionally also for detecting an orientation of the sensor means, and generating at least a signal comprising information about detected movements of the animal and optionally also comprising information about detected orientations, a control unit for processing the information in the signal and for storing the processed information, and transmitting means for transmitting information stored in the control unit, wherein the control unit is arranged to carry out the method according to the invention with the device.

Figure 2:
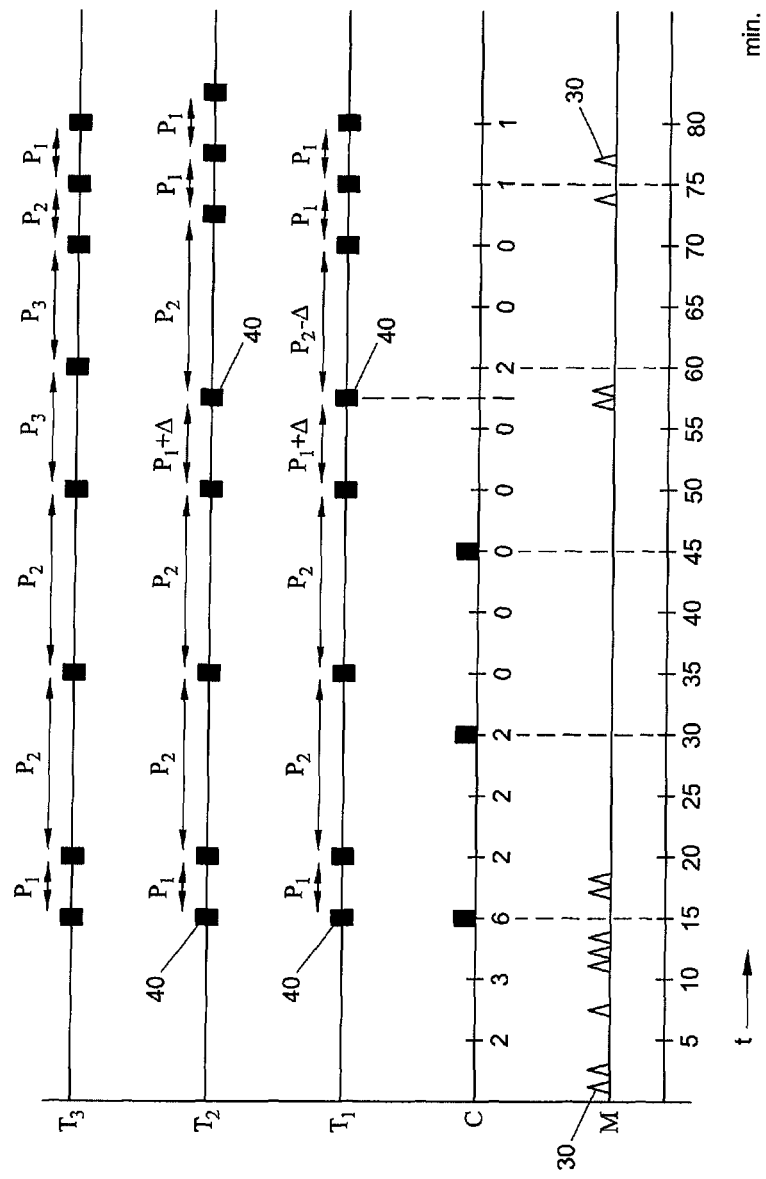

The invention will be further elucidated with reference to the drawings, in which:

FIG. 1 shows a device 1 according to the invention for carrying out a method according to the invention; and FIG. 2 shows a time diagram in which different embodiments are shown for carrying out a method according to the invention.

In FIG. 1 reference numeral 1 denotes a device for carrying out a method according to the invention. The device is provided with sensor means 2 for detecting movements of an animal. The sensor means 2 are implemented as sensor means known per se, such as, for example, a sensor as described in European patent application EP 1 949 035 or a G-sensor, known per se. In this example, the sensor means are implemented as a G-sensor, known per se, which is capable of measuring accelerations in three dimensions and is also capable of measuring the orientation of the sensor with respect to the earth's surface.

The device is further provided with a control unit 4 which is coupled with the sensor means via a signal line 6. The control unit is arranged for processing information in a signal which is generated with the aid of the sensor means 2. This signal comprises information about detected movements of the animal and optionally also information about detected orientations of the sensor means (and hence orientations of the animal when the device is attached to the animal). The control unit is arranged for processing the information in the signal for storing the processed information.

The device is further provided with transmitting means 10 which are connected to the control unit via a signal line 8, for transmitting information stored in the control unit.

The device is further provided with a battery 12 which in this example is connected to the control unit 4 via a line 14, for supplying energy to the control unit, the sensor means 2 and the transmitting means 10. The transmitting means 10 in this example are active transmitting means having a transmission frequency which is in the UHF band. The device is, for example, furthermore provided with a resonant circuit 18 (as known for RFID) which is connected via a line 16 to the control unit 4.

A signal transmitted with the aid of the transmitting means 10 is received, in this example, with the aid of a receiver 20. The receiver 20 is connected to a computer system 22 to which the received information is supplied for further processing and for storage. Also connected to the computer 22 is a reader 24 for transmitting an electromagnetic interrogation field. When the resonant circuit 18 is introduced into the electromagnetic interrogation field 24, it responds by, for example, transmitting information which is stored in the control unit 4. Suffice it to note here that the resonant circuit 18 will obtain its energy for operation from the electromagnetic interrogation field transmitted with the aid of the reader 24. The transmitter 10, by contrast, obtains its energy from the energy source 12.

In use, the control unit controls the device according to a method according to the invention such as it will be set out hereinafter, partly with reference to FIG. 2.

In FIG. 2 along the horizontal axis time is plotted in minutes. In this example, the device is attached to the leg of an animal. In this example, the device is arranged to detect movements of a predetermined type in the form of steps of the animal. In FIG. 2 it is indicated with the diagram M when the animal makes a step. A step is indicated in the diagram with a pulse 30. Thus, it appears, for example, that in the period running from 0-5 minutes, the animal makes two steps.

The control unit 4 provides that at periodically repeated moments the signal determined with the aid of the sensor means is registered (step a.). In this example, every 0.5 seconds the signal of the sensor means is registered. In fact, this amounts to a sampling of the signal with a sampling frequency of 0.5 seconds. This period of 0.5 seconds is so short as to allow every step to be registered in this way. The sampled signal can then have a shape as denoted with M in FIG. 2.

The signal M is divided up by the control unit into first predetermined periods, with each first period in this example having a length of 5 minutes. Also, it holds in this example that the first predetermined periods are contiguous to each other. In this example, a first first predetermined period runs from 0-5 minutes, a second first predetermined period from 5-10 minutes, a third first predetermined period from 10-15 minutes, etc. The control unit detects the movements of the predetermined type and determines the number of movements of the predetermined type that have occurred during a first period (step b.). Next, this is repetitively carried out for each first period (step c.). In this example, the result for determining the number of movements of the predetermined type is indicated in diagram C of FIG. 2. Thus, it can be seen that at the end of the first first predetermined period running from 0-5 minutes, two movements have been detected. It can also be seen that during the second first predetermined period running from 5-10 minutes, one movement has been detected. This is indicated in this example with a 3 because the 3 reflects the total number of movements detected in the first period from 0-5 minutes and in the first period from 5-10 minutes. Also, it becomes clear that the control unit in the first period running from 10-15 minutes has detected three movements of the predetermined type. This is indicated in this example with a 6 because the detected movements of the first period running from 0-5 minutes and the first period running from 5-10 minutes are counted in. Next, the number of predetermined-type movements which have been counted during a predetermined set of periods which comprises a number of successive periods is stored in the control unit. In this example the predetermined set of periods each time comprises three successive first periods. In other words, for the three first periods which are between 0-15 minutes, the number 6 is stored. For the next first period, running from 15-20 minutes, again the number of movements are detected. In this example, this concerns two movements of the predetermined type of the animal. Thus, at a time t=20 minutes, for the first period running from 15-20 minutes two movements have been detected. For the period running from 20-25 minutes no movements are detected, etc. In this manner, for each first period, movements of the predetermined type are detected and counted. This is denoted with a method step b. which is thus carried out for a multiplicity of successive predetermined periods (step c.). Next, as already set out above, in a method step d. there is stored in the control unit the number of predetermined-type movements counted in a predetermined set of periods which, in this example, in each case comprises three successive first periods. This step, too, is repeated for successive predetermined sets of three periods each (step e.). This means in this example that after the number of detected movements for the set of first periods between 0-15 minutes has been stored (in this example 6), for the next set of three successive first periods which in this example are between 15-30 minutes, the number 2 is stored. Furthermore, as can be seen in FIG. 2, for the third set of first periods which are between 30-45 minutes, the number 0 is stored. Also, for the fourth set of first periods, which are between 45-60 minutes, the number 2 is stored. Furthermore, for the fifth set of first periods, which are between 60-75 minutes, the number 1 is stored.

The control unit provides furthermore that step f. is carried out, which involves the transmission of a number of the stored numbers of counted movements. In this example, this works as follows. The transmission of a number of the stored numbers of counted movements is carried out at moments that depend on the number of detected predetermined-type movements in at least one of the past first periods. In this regard, it holds in this example that the length of a second period between two successive moments at which stored numbers of counted movements are transmitted in dependence on the number of detected predetermined-type movements in at least one of the past first periods can vary from a first duration to a second duration, with the second duration being greater than the first duration. In this example, the first duration is 5 minutes and the second duration is 15 minutes.

More particularly, this means that in this example step f. is carried out following a second period having a length equal to the second duration, i.e., 15 minutes, if in this second period no movements of the predetermined type have been detected. Also, it holds that step f. is carried out following a second period of a length equal to the first duration, in this example 5 minutes, if in this second period at least one movement of the predetermined type has been detected.

In this example we assume that the device has already been in operation for some time and that this has resulted in a step f. being carried out at time t=15 minutes, i.e., at time t=15 minutes information about stored numbers of detected movements as discussed above has been transmitted. This is reflected in the example according to diagram T2 by the cube 40. So, with the cube 40 it is denoted that a step f. is carried out in which information is transmitted with the aid of the transmitter 10. Because in a second period starting from time t=15 minutes, within 5 minutes two movements have been detected, step f. is also carried out 5 minutes after the last transmission has occurred.

This means that from t=20 minutes, a new second period starts to run. Because between t=20 minutes and t=35 minutes no movements at all have been detected, the second period presently has a duration equal to the second duration, i.e., 15 minutes. Entirely analogously, it holds that the second period running from 35 minutes to 50 minutes has a duration of 15 minutes because in this whole second period no movements have been detected.

It holds therefore, as discussed above, that step f. is carried out following a second period having a length equal to the second duration and in which no movements of the predetermined type have been detected and that step f. is also carried out following a second period having a length equal to the first duration and in which at least one movement of the predetermined type has been detected.

It holds furthermore that step f. is always carried out at the moment when a movement of the predetermined type has been detected while during a period preceding the moment which is longer than the first duration no step f. has been carried out. This occurs, for example, at time t=57 minutes. At time t=57 minutes, for a period longer than the first duration, i.e., a period longer than 5 minutes, no transmission has taken place. In fact, the last transmission occurred at time t=50 minutes. When at time t=57 minutes a movement is detected, then, directly at the moment when the respective movement is detected, step f. is carried out. The carrying out of step f., i.e., the respective transmission with the transmitter unit 10, is again indicated with a cube 40.

Presently, it holds that at time t=57 minutes a new second period starts to run. Eventually, this second period will have a length of 15 minutes because during this whole second period no movements are detected. The next transmission will therefore occur at time t=57 minutes+15 minutes=t=72 minutes.

All transmissions that have been described hereinabove are carried out with the aid of the transmitter 10. Moreover, it holds in this example that with the transmission in step f., also transmission of an identification code stored in the control unit is carried out. Furthermore, it holds in this example that in step f. a multiplicity of stored numbers of counted movements of the predetermined type are transmitted, while the movements that are transmitted, in this example, relate to a period of the last 24 hours. This means that when, for instance, as in this example, at time t=50 minutes step f. is carried out, not only the number 0 is transmitted which belongs to time t=45 minutes, but also the number 2 is transmitted which belongs to time t=30 minutes, the number 6 is transmitted which belongs to time t=15 minutes, etc. Thus, all counted movements, in each case relating to three successive first periods, that have been determined in the past 24 hours are transmitted. To the transmitted number of counted movements, an indicator is added which indicates to what period or to what time the respective number of counted movements relates. Thus, for example, in the transmission at t=50 minutes it is indicated that the 0 relates to an age of 5 minutes, the 2 relates to an age of 20 minutes, the 6 relates to an age of 35 minutes, etc. Of course, the point in time to which numbers of counted movements relate can also be denoted in other manners, for example, an absolute time indication may be used when the control unit is provided with an internal clock tracking time and date.

In the diagram denoted T1 in FIG. 2, a possible alternative embodiment of the method is reflected. Below, only the difference with respect to the method according to T2 will be discussed. The difference resides in the feature that the method is carried out such that each beginning of a second period coincides with the beginning of a first period. After carrying out the steps f. at times t=15 minutes, 20 minutes, 35 minutes, 50 minutes and 57 minutes according to diagram T1 (according to the same mechanism as discussed for diagram T2), however, after transmission of information at time t=57 minutes, a switch is made back to transmission at moments each coinciding with the beginning of a first period. It holds, therefore, that after carrying out the step f. at time t=57 minutes, a next second period, which on the basis of detected movements would have a length equal to the first duration (5 minutes) or the second duration (15 minutes), is just sufficiently shortened for the beginning of a new second period to coincide with the beginning of a first period. In FIG. 2 this means that the second period following after t=57 minutes would originally have a length of 15 minutes and is presently shortened by a duration Δ which ensures that the next transmission occurs at the beginning of the first period, in this case at time t=70 minutes. The shortening of the second period by the amount Δ corresponds to the amount Δ by which the first period lying between time t=50 minutes and t=57 minutes has been lengthened with respect to the first duration T=5 minutes. From time t=70 minutes the method proceeds again as described above. So, then it holds again that step f. is carried out following a second period having a length equal to the second duration (15 minutes) if in this second period of a length equal to the second duration no movements of the predetermined type have been detected. Also, it holds that step f. is carried out again following a second period having a length equal to the first duration if in this second period having a length equal to the first duration at least one movement of the predetermined types has been detected. Also, it holds again that step f. is always carried out again at a moment when a movement of the predetermined type has been detected while no step f. has been carried out during a period preceding the moment which is longer than the first duration.

Referring to diagram T3, a third variant according to a method according to the invention will now be discussed. The difference with respect to the variant according to diagram T2 is that presently it does not hold that step f. is always carried out at a moment when a movement of the predetermined type has been detected while no step f. has been carried out during a period preceding the moment which is longer than the first duration. A direct consequence of this is that the second period can have a length of 5 minutes, 10 minutes or 15 minutes, since the carrying out of step f. at the times t=15, 35, 50 remains the same. Presently, however, it holds that at time t=57 a movement is detected. According to this variant, it holds that step f. is also carried out following the second period having a length which is equal to one or more times the first duration and which is smaller than the second duration while in this second period at least one movement of the predetermined type has been detected. In the present case, this means that presently the method step f. is carried out at time t=60 minutes, the second period in that case having a length of 10 minutes. Because subsequently at time t=73 minutes again a movement is detected, method step f. in turn is again carried out at a time t=75 minutes. Similarly, the method step is also carried out again at a time t=80 because at time t=77 minutes a movement of the predetermined type was registered. Such variants are each understood to be within the purview of the invention.

The invention is in no way limited to the exemplary embodiments outlined above. Thus, it is possible, for example, that in each of the exemplary embodiments according to T1, T2, or T3 a variant is applied in which the first duration and/or the second duration are randomly chosen. Below, it will be indicated for each of the exemplary embodiments T1, T2, and T3 how this can be implemented in the respective embodiments.

It holds for each variant according to T1, T2, or T3 with the random selection referred to that at least one of the first duration and the second duration is randomly selected by the control unit, with the respective selection taking place each time after step f. has been carried out. In this example, then, with each variant according to T1, T2, or T3 (with the randomly chosen first and second duration) each time when step f. has been carried out, a selection is made for the first duration and the second duration. In this example, this selection is carried out such that this first duration is within a predetermined first range. This first range in this example is equal to 3-7 minutes. Furthermore, the selection is carried out such that the second duration is in a range of 10-20 minutes. It thus holds that the minimum length of a second period can vary randomly from 3-7 minutes, this minimum length being chosen each time after step f. has been carried out. Also, it thus holds that the maximum length of a second period can vary randomly from 10-20 minutes, this maximum length being chosen each time after step f. has been carried out. Accordingly, after step f. has been carried out, it is fixed, for example, that the first duration is 4 minutes. The second duration in this example then equals 17 minutes. Entirely analogously to what has been discussed above, in each variant (with the randomly chosen first and second duration) according to T1, T2, or T3, step f. can then be carried out following a second period ending at a moment when it holds that in a period immediately preceding that moment having a length equal to the second duration, no movements of a predetermined type have been detected. Entirely analogously to what has been discussed above, in each variant (with the randomly chosen first and second duration) according to T1 or T2, step f. can then also be carried out following a second period ending at a moment when in a period preceding that moment having a length equal to the first duration, movements of a predetermined type have been detected. Entirely analogously to what has been discussed above, in the variant according to T3 (with the randomly chosen first and second duration), step f. can then also be carried out following the second period ending at a moment when in a period preceding that moment having a length which is equal to one or more times the first duration and which is smaller than the second duration, at least one movement of the predetermined type has been detected.

After carrying out step f., in this example, for the variants according to T1, T2, or T3 (with the randomly chosen first and second duration) again a new first duration and a new second duration are selected. Entirely analogously to what has been discussed above, it holds in this example for each variant according to T1, T2, or T3 (with the randomly chosen first and second duration) that the method step f. is not carried out anymore if during a third period having a predetermined length which is longer than the length of any second period, no movements of a predetermined type have been detected. The third period can, for example, again have a length of 8 hours. This 8-hour period is then indeed longer than any possible second period, which, after all, is always less than 20 minutes.

Also, it holds in this example for each variant according to T1 or T2 (with the randomly chosen first and second duration) that step f. is always carried out at a moment when a movement of the predetermined type is detected, while during a period preceding the moment which is longer than the longest possible first duration no step f. has been carried out. The longest possible first duration for the variants according to T1, T2, or T3 (with the randomly chosen first and second duration) is 7 minutes in this example. In particular, it holds here according to the variant according to T1 (with the randomly chosen first and second duration) that the moments at which a second period starts each lie within a range around a moment at which a first period starts, the first periods each having a same duration.

Also for each of the variants according to T1, T2, or T3 (with the randomly selected first and second duration) it holds that in step d. a set comprises three successive first periods. Also, it holds that with the transmission in step f., also transmission of an identification code stored in the control unit is carried out. Such variants are each understood to be within the purview of the invention.

Furthermore, in each of the examples given (with or without the randomly selected first and second duration) it further holds that the movement of a predetermined type concerns a step of an animal. However, the device may also be configured, for example, to be attached to the neck of the animal, the movement of a predetermined type then involving a movement of the head or neck of the animal. Such types of movements can be recognized in manners known per se.

The invention claimed is:

1. A method for monitoring movements of an animal, wherein the animal is provided with a device with a sensor for detecting movements of the animal and generating at least a signal comprising information about detected movements of the animal, a control unit for processing the information in the signal and for storing the processed information and a transmitter for transmitting information stored in the control unit, wherein the method comprises the following method steps:
   a. at periodically repeated moments, registering with the control unit the signal determined with the sensor;
   b. on the basis of signals registered during a first predetermined period which comprises a multiplicity of method steps a., detecting with the control unit movements of a predetermined type and determining a number of movements of the predetermined type that occurred during the first predetermined period;
   c. repeating the method step b. for a multiplicity of successive first predetermined period;
   d. storing in the control unit the number of predetermined-type movements counted during a predetermined set of periods which comprises a number of successive first predetermined periods in combination with storing at least one orientation of the sensor which has been measured during the predetermined number of successive first predetermined periods of the set;
   e. repeating step d. for successive predetermined sets of first predetermined periods;
   f. transmitting a number of stored numbers of counted movements at moments which depend on the number of detected predetermined-type movements in at least one of past first predetermined periods and depend on at least one of the stored orientations of the sensor;
   characterized in that a length of a second period between successive moments at which stored numbers of counted movements are transmitted in dependence on the detected number of movements of the predetermined-type in at least one of past first predetermined periods and in dependence on at least one of the stored orientations of the sensor varies from a first duration to a second duration, with the second duration being greater than the first duration.

2. The method according to claim 1, characterized in that the first duration is predetermined and that the second duration is predetermined, while in particular the second duration is equal to or less than three times the first duration.

3. The method according to claim 2, characterized in that the first duration and the second duration are each fixed.

4. The method according to claim 1, characterized in that a duration of each first predetermined period is fixed.

5. The method according to claim 3, characterized in that a duration of each first predetermined period is equal to the first duration.

6. The method according to claim 3, characterized in that the first duration is about 5 minutes and that the second duration is about 15 minutes.

7. The method according to claim 1, characterized in that step f. is carried out following a second period having a length equal to the second duration if in this second period having a length equal to the second duration no movements of the predetermined type is detected, wherein step f. is carried out following a second period having a length equal to the first duration if in this second period having a length equal to the first duration at least one movement of the predetermined type is detected or wherein step f. is carried out following the second period having a length which is equal to one or more times the first duration and which is less than the second duration while in this second period at least one movement of the predetermined type is detected.

8. The method according to claim 7, characterized in that the method step f. is not carried out if during a third period having a predetermined length which is longer than the second duration no movements of the predetermined type is detected.

9. The method according to claim 8, characterized in that the third period has a length of 2-24 hours, 4-12 hours, 6-10 hours, or 8 hours.

10. The method according to claim 7, characterized in that step f. is carried out at a moment when a movement of the predetermined type is detected while during a period preceding the moment which is longer than the first duration no step f. is carried out.

11. The method according to claim 1, characterized in that a beginning of a second period coincides with the beginning of a first predetermined period.

12. The method according to claim 1, characterized in that successive first predetermined periods are contiguous to each other.

13. The method according to claim 1, characterized in that at least one of the first duration and the second duration is randomly selected by the control unit, with the selection taking place each time after step f. is carried out.

14. The method according to claim 13, characterized in that selection of the first duration is within a predetermined first range and the selection of the second duration is within a predetermined second range.

15. The method according to claim 14, characterized in that the first range is equal to 3-7 minutes and that the second range is equal to 10-20 minutes.

16. The method according to claim 13, characterized in that step f. is carried out following a second period which ends at a moment when it holds that in a period directly preceding that moment having a length equal to the second duration no movements of the predetermined type is detected, wherein step f. is also carried out following a second period which ends at a moment when in a period preceding that moment having a length equal to the first duration at least one movement of the predetermined type is detected or wherein step f. is also carried out following the second period which ends at a moment when in a period preceding that moment having a length which is equal to one or more times the first duration and which is less than the second duration at least one movement of the predetermined type is detected.

17. The method according to claim 16, characterized in that the method step f. is not carried out if during a third period having a predetermined length which is longer than the length of a second duration no movements of the predetermined type is detected.

18. The method according to claim 17, characterized in that the third period has a length of 2-24 hours, 4-12 hours, 6-10 hours, or 8 hours.

19. The method according to claim 16, characterized in that step f. is carried out at a moment when a movement of the predetermined type is detected while during a period preceding the moment which is longer than a longest first duration when no step f. is carried out.

20. The method according to claim 13, characterized in that the moments at which a second period starts are each within a range around a moment at which a first predetermined period starts, the first predetermined periods each having a same duration.

21. The method according to claim 1, characterized in that the method step f. is not carried out if during a fourth period having a predetermined length which is longer than the length of a second period detected that the sensor assumes a predetermined orientation.

22. The method according to claim 1, characterized in that in step d. a set comprises three successive first predetermined periods.

23. The method according to claim 1, characterized in that in step f., the transmission of an identification code stored in the control unit is carried out.

24. The method according to claim 1, characterized in that a movement of the predetermined type which is detected in step b. is a predetermined movement, which is a step of the animal or a movement of a head or neck of the animal.

25. The method according to claim 1, characterized in that in step f. a multiplicity of the stored numbers of counted movements of the predetermined type are transmitted.

26. The method according to claim 10, wherein a next second period is shortened in order that the beginning of a new second period coincides with a beginning of a first predetermined period.

27. The method according to claim 19, wherein a nest second period has a length equal to the first duration or the second duration and is shortened in order that a beginning of a new second period coincides with the beginning of a first predetermined period.

28. A device for monitoring a movement of an animal, wherein the device is arranged to be attached to the animal and is provided with sensor for detecting movements of the animal, and generating at least a signal comprising information about detected movements of the animal, a control unit for processing the information in the signal and storing the processed information and a transmitter for transmitting information stored in the control unit, wherein the control unit is arranged to carry out the method according to claim 1 with the device.

29. The method according to claim 1, wherein the sensor detects an orientation of the sensor and generates at least one signal comprising information about detected orientations; wherein, in step d., a number of predetermined-type movements counted during the predetermined sets of first predetermined periods which comprises the number of successive first predetermined periods in combination with at least one orientation of the sensor which is measured during the predetermined number of successive first predetermined periods of the predetermined sets of first predetermined periods are stored in the control unit; and wherein, in step f., the number of the stored numbers of counted movements is transmitted at moments which depend on the number of detected predetermined-type movements in at least one of a past first predetermined period and depend on at least one of the stored orientations of the sensor.

30. The method according to claim 29, characterized in that a length of a second period between successive moments at which stored numbers of counted movements are transmitted in dependence on the detected number of movements of the predetermined-type in at least one of the past first predetermined periods and in dependence on at least one of the stored orientations of the sensor varies from a first duration to a second duration, with the second duration being greater than the first duration.

31. The method according to claim 21, wherein the predetermined orientation corresponds to an orientation of the sensor when the animal is lying.

32. The device according to claim 28, wherein the sensor detects an orientation of the sensor and generates the at least one signal comprising information about detected orientations.

33. The method according to claim 1, characterized in that in step f. a multiplicity of the stored numbers of counted movements of the predetermined type are transmitted wherein the number relates to one of a total past period having a length of one of 12-26 hours and a total period of 24 hours.

34. A method for monitoring movements of an animal, wherein the animal is provided with a device provided with a sensor for detecting movements of the animal also for detecting an orientation of the sensor and generating at least a signal comprising information about detected movements of the animal and optionally also comprising information about detected orientations, a control unit for processing the information in the signal and for storing the processed information and a transmitter for transmitting information stored in the control unit, wherein the method comprises the following method steps:
   a. at periodically repeated moments, registering with the control unit the signal determined with the sensor;
   b. on the basis of signals registered during a first predetermined period which comprises a multiplicity of method steps a., detecting with the control unit movements of a predetermined type and determining a number of movements of the predetermined type that occurred during the first predetermined period;
   c. repeating the method step b. for a multiplicity of successive first predetermined periods;
   d. storing in the control unit the number of predetermined-type movements counted during a predetermined set of periods which comprises a number of successive first predetermined periods in combination with storing at least one orientation of the sensor which has been measured during the predetermined number of successive first predetermined periods of the set;
   e. repeating step d. for successive predetermined sets of first predetermined periods;
   f. transmitting a number of stored numbers of counted movements at moments which depend on at least one of the stored orientations of the sensor;

characterized in that a length of a second period between successive moments at which stored numbers of counted movements are transmitted in dependence on at least one of the stored orientations of the sensor varies from a first duration to a second duration, with the second duration being greater than the first duration.

35. The method according to claim 34, characterized in that the first duration is predetermined and that the second duration is predetermined, while the second duration is equal to or less than three times the first duration.

36. The method according to claim 35, characterized in that the first duration and the second duration are each fixed.

37. The method according to claim 34, characterized in that a duration of each first predetermined period is fixed.

38. The method according to claim 37, characterized in that a duration of each first predetermined period is equal to the first duration.

39. The method according to claim 36, characterized in that the first duration is about 5 minutes and that the second duration is about 15 minutes.

40. The method according to claim 34, characterized in that step f. is carried out following a second period having a length equal to the second duration if in this second period having a length equal to the second duration no movements of the predetermined type is detected, wherein step f. is carried out following a second period having a length equal to the first duration if in this second period having a length equal to the first duration at least one movement of the predetermined type is detected and/or wherein step f. is carried out following the second period having a length which is equal to one or more times the first duration and which is less than the second duration while in this second period at least one movement of the predetermined type is detected.

41. The method according to claim 40, characterized in that the method step f. is not carried out if during a third period having a predetermined length which is longer than the second duration no movements of the predetermined type is detected.

42. The method according to claim 41, characterized in that the third period has a length of one of 2-24 hours, 4-12 hours, 6-10 hours and 8 hours.

43. The method according to claim 40, characterized in that step f. is carried out at a moment when a movement of the predetermined type is detected while during a period preceding the moment which is longer than the first duration no step f. is carried out.

44. The method according to claim 34, characterized in that a beginning of a second period coincides with a beginning of a first predetermined period.

45. The method according to claim 34, characterized in that successive first predetermined periods are contiguous to each other.

46. The method according to claim 34, characterized in that at least one of the first duration and the second duration is randomly selected by the control unit, with the selection taking place each time after step f. is carried out.

47. The method according to claim 46, characterized in that the selection of the first duration is within a predetermined first range and the selection of the second duration is within a predetermined second range.

48. The method according to claim 47, characterized in that the first range is equal to 3-7 minutes and that the second range is equal to 10-20 minutes.

49. The method according to claim 46, characterized in that step f. is carried out following a second period which ends at a moment when it holds that in a period directly preceding that moment having a length equal to the second duration no movements of the predetermined type is detected, wherein step f. is carried out following a second period which ends at a moment when in a period preceding that moment having a length equal to the first duration at least one movement of the predetermined type is detected or wherein step f. is carried out following the second period which ends at a moment when in a period preceding that moment having a length which is equal to one or more times the first duration and which is less than the second duration at least one movement of the predetermined type is detected.

50. The method according to claim 49, characterized in that the method step f. is not carried out if during a third period having a predetermined length which is longer than the length of a second duration no movements of the predetermined type is detected.

51. The method according to claim 50, characterized in that the third period has a length of one of 2-24 hours, 4-12 hours, 6-10 hours and 8 hours.

52. The method according to claim 49, characterized in that step f. is carried out at a moment when a movement of the predetermined type is detected while during a period preceding the moment which is longer than a longest first duration no step f. is carried out.

53. The method according to claim 46, characterized in that the moments at which a second period starts are each within a range around a moment at which a first predetermined period starts, the first predetermined periods each having a same duration.

54. The method according to claim 34 characterized in that the method step f. is not carried out if during a fourth period having a predetermined length which is longer than the length of a second period it is detected that the sensor assumes a predetermined orientation.

55. The method according to claim 54, characterized in that the predetermined orientation corresponds to an orientation of the sensor when the animal is lying.

56. The method according to claim 34, characterized in that in step d. a set comprises three successive first predetermined periods.

57. The method according to claim 34, characterized in that in step f., the transmission of an identification code stored in the control unit is carried out.

58. The method according to claim 34, characterized in that a movement of the predetermined type which is detected in step b. is a predetermined movement, which is a step of the animal or a movement of a head or neck of the animal.

59. The method according to claim 34, characterized in that in step f. a multiplicity of the stored numbers of counted movements of the predetermined type are transmitted.

60. The method according to claim 43, wherein a next second period is shortened in order that the beginning of a new second period coincides with a beginning of a first predetermined period.

61. The method according to claim 52, wherein a next second period has a length equal to the first duration or the second duration and is shortened in order that a beginning of a new second period coincides with the beginning of a first predetermined period.

* * * * *